(12) United States Patent
McCabe et al.

(10) Patent No.: US 10,953,561 B2
(45) Date of Patent: *Mar. 23, 2021

(54) SYSTEMS AND METHODS FOR CUTTING OR PERFORATING A WEB MATERIAL

(71) Applicant: Curt G. Joa, Inc., Sheboygan Falls, WI (US)

(72) Inventors: John A. McCabe, Sheboygan Falls, WI (US); Jeff Middlesworth, Sheboygan, WI (US); Darren Horness, Sheboygan, WI (US); Peter Jenquin, Plymouth, WI (US); Gottfried J. Hohm, Oconomowoc, WI (US); Daniel A. Peterson, Sheboygan, WI (US); Sudeep Ingole, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/424,587

(22) Filed: May 29, 2019

(65) Prior Publication Data
US 2019/0275692 A1 Sep. 12, 2019

Related U.S. Application Data

(60) Continuation of application No. 15/864,664, filed on Jan. 8, 2018, now Pat. No. 10,391,660, which is a (Continued)

(51) Int. Cl.
*B26D 7/01* (2006.01)
*B26F 3/00* (2006.01)
(Continued)

(52) U.S. Cl.
CPC ........ *B26D 7/015* (2013.01); *A61F 13/15707* (2013.01); *A61F 13/15723* (2013.01); *B26D 7/018* (2013.01); *B26F 1/08* (2013.01); *B26F 3/004* (2013.01); *B26F 3/02* (2013.01); *B26F 3/12* (2013.01); *B65H 29/241* (2013.01);
(Continued)

(58) Field of Classification Search
CPC .... B65H 35/0073; B65H 35/08; B65H 39/14; B65H 2301/33216; B65H 2406/3452; B65H 2406/3612; B65H 2801/57; A61F 13/15723; A61F 13/15764; A61F 13/15707; B26D 1/425; B26D 7/018; B26D 7/015; Y10T 83/14; B26F 3/004
See application file for complete search history.

(56) References Cited

U.S. PATENT DOCUMENTS 3,355,974 A  12/1967 Carmichael
3,491,651 A  1/1970 Pascoe
(Continued)

*Primary Examiner* — Omar Flores Sanchez
(74) *Attorney, Agent, or Firm* — Ziolkowski Patent Solutions Group, SC

(57) ABSTRACT

Systems and methods utilizing stationary and/or moveable cutting components provide limited interference with web processing operations, such as pad spin and pitch alteration. Heat, laser, fluid, or mechanical cutting operations may be used, including respectively, a heated element (e.g., wire, ribbon, bar, or embossing or perforating element) that may be triggered inductively, water or steam jets, or improved knife/anvil cooperation.

19 Claims, 10 Drawing Sheets

Related U.S. Application Data division of application No. 15/159,313, filed on May 19, 2016, now Pat. No. 9,862,112.

(60) Provisional application No. 62/164,939, filed on May 21, 2015.

(51) Int. Cl.
| | |
|---|---|
| *B26F 3/12* | (2006.01) |
| *B26F 1/08* | (2006.01) |
| *B26F 3/02* | (2006.01) |
| *A61F 13/15* | (2006.01) |
| *B65H 29/24* | (2006.01) |
| *B65H 35/00* | (2006.01) |
| *B65H 39/14* | (2006.01) |
| *B26D 1/143* | (2006.01) |
| *B26D 1/16* | (2006.01) |
| *B26D 1/20* | (2006.01) |
| *B26D 7/08* | (2006.01) |
| *B65H 5/12* | (2006.01) |
| *B65H 5/14* | (2006.01) |

(52) U.S. Cl.
CPC ......... *B65H 35/0086* (2013.01); *B65H 39/14* (2013.01); *B26D 1/1435* (2013.01); *B26D 1/165* (2013.01); *B26D 1/205* (2013.01); *B26D 7/086* (2013.01); *B65H 5/12* (2013.01); *B65H 5/14* (2013.01); *B65H 2301/33216* (2013.01); *B65H 2301/5153* (2013.01); *B65H 2301/51533* (2013.01); *B65H 2301/51534* (2013.01); *B65H 2403/511* (2013.01); *B65H 2406/345* (2013.01); *B65H 2406/3454* (2013.01); *B65H 2406/3612* (2013.01); *B65H 2801/57* (2013.01)

(56) References Cited

U.S. PATENT DOCUMENTS

| | | | |
|---|---|---|---|
| 3,707,102 | A | 12/1972 | Huppenthal |
| 4,380,484 | A | 4/1983 | Repik et al. |
| 5,520,875 | A * | 5/1996 | Wnuk ............... A61F 13/00991 264/504 |
| 5,735,984 | A | 4/1998 | Hoff et al. |
| 5,879,494 | A | 3/1999 | Hoff et al. |
| 6,296,469 | B1 | 10/2001 | Suzuki |
| RE38,033 | E | 3/2003 | Okonski et al. |
| 2003/0167888 | A1 * | 9/2003 | Thomsen ................ B26D 3/10 83/35 |
| 2004/0007329 | A1 | 1/2004 | Gill et al. |
| 2008/0289468 | A1 | 11/2008 | Nakakado et al. |
| 2011/0030697 | A1 * | 2/2011 | Thompson ............. B26D 7/018 128/844 |
| 2012/0145334 | A1 | 6/2012 | Pallot et al. |
| 2013/0000458 | A1 * | 1/2013 | Ueda ............... H01M 10/0585 83/367 |
| 2015/0083309 | A1 * | 3/2015 | Long ................ B29C 66/83517 156/161 |
| 2015/0118942 | A1 * | 4/2015 | Hashish .................. B26F 3/004 451/80 |
| 2015/0197030 | A1 * | 7/2015 | Fry ........................... G01N 1/06 83/24 |
| 2017/0129120 | A1 | 5/2017 | McCabe et al. |

* cited by examiner

SYSTEMS AND METHODS FOR CUTTING OR PERFORATING A WEB MATERIAL

CROSS-REFERENCE TO RELATED APPLICATIONS

This application is a continuation of and claims priority to co-pending U.S. patent application Ser. No. 15/864,664, filed 1 Jan. 2018, which is a division of U.S. patent application Ser. No. 15/159,313, filed 19 May 2016, now U.S. Pat. No. 9,862,112, which claims the benefit of U.S. provisional application Ser. No. 62/164,939, filed 21 May 2015, the disclosures of which are incorporated herein by reference in their entirety.

BACKGROUND OF THE INVENTION

Embodiments of systems and methods according to the present invention relate generally to web or sheet material processing, and more particularly to cutting or perforating such materials along or across a machine direction. This invention relates to a method and apparatus for receiving and cutting or perforating a continuous web, and transferring articles, or inserts, such as absorbent pads cut or otherwise separated from the web in the manufacture of disposable absorbent articles such as diapers, incontinence control garments or female sanitary pads as they advance along a production line.

Prior systems and methods normally cut a received web, at a nip formed by a knife cooperating with an anvil, to form the pad prior to or contemporaneously with placement on a transfer mechanism. However, the cooperation of a knife with an anvil can be complicated in situations requiring particular translation of a cut pad in systems imparting spin and/or pitch modification (i.e., pad spacing modification).

SUMMARY OF THE INVENTION

Briefly, in accordance with a preferred embodiment thereof, provided are an apparatus and a method for receiving a continuous web and separating a section from the web thereby forming a pad. The apparatus and method may further be used for spinning the pad to a predetermined angle and/or changing the spacing between neighboring pads while transferring the pad to a receiving surface.

In a preferred embodiment of the present invention, the apparatus generally includes a transfer mechanism and a cutter. The transfer mechanism comprises a plurality of pucks rotatably driven about a transfer axis. The cutter comprises a heated element (e.g., wire, ribbon, bar, or embossing or perforating element), one or a plurality of fluid jets, or an improved anvil roller and a plurality of knife blades rotatably driven about a knife blade axis. The pucks are each supported by a puck support. If spin and spacing of pucks is to be provided, each puck is coupled to a spin cam and a pitch cam. As the puck rotates about the transfer axis, the cams alter the position of the puck. The spin cam alters puck motion about a puck spin axis which is generally perpendicular to the transfer axis. The pitch cam alters the relative circumferential spacing of adjacent pucks.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
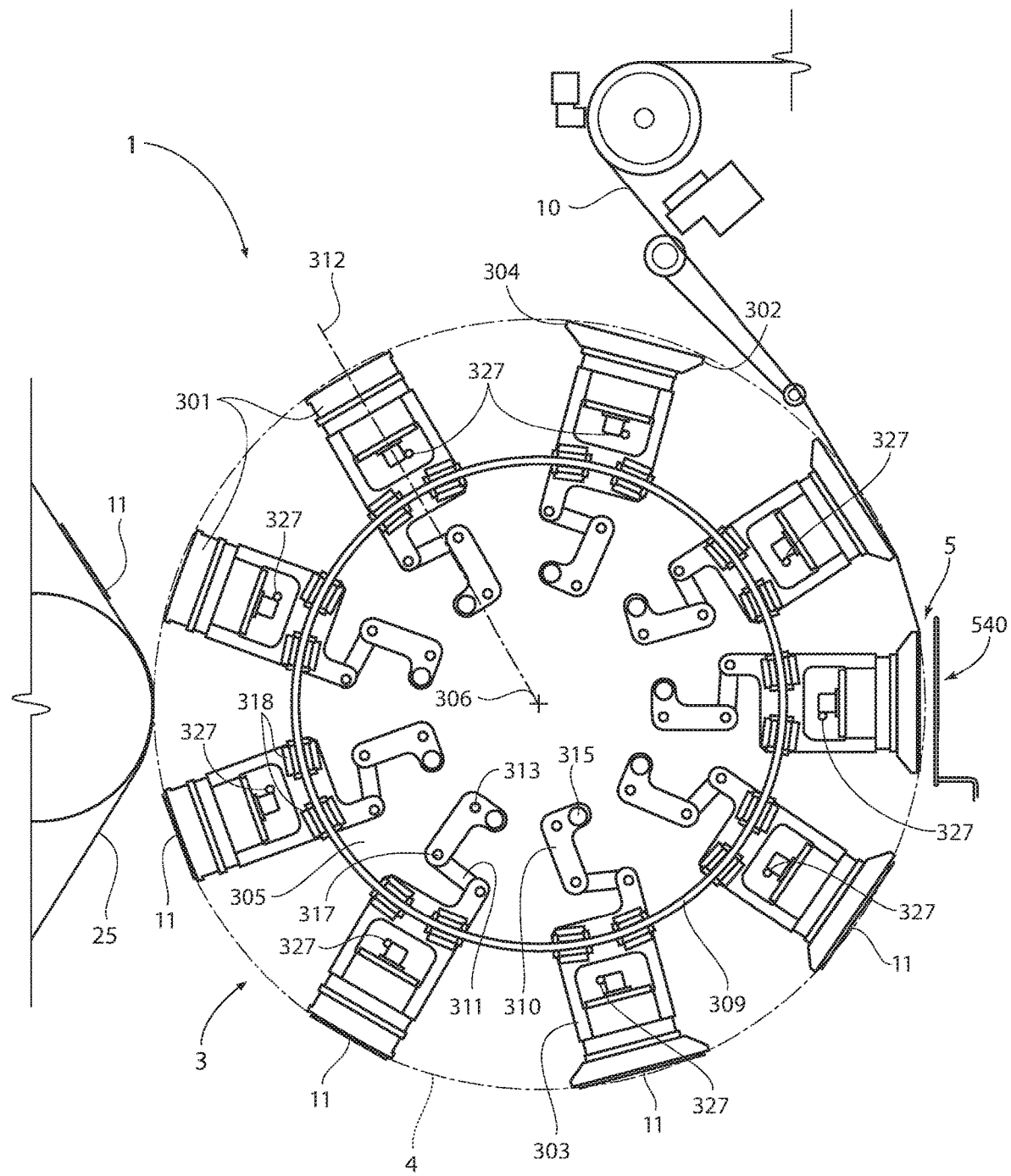
FIG. 1 is a front elevation view of a first embodiment of an apparatus according to the present invention.

Generally, systems and methods according to the present invention relate to the processing of singular or composite web materials. As is known in the art, a web may be transported to an apparatus, a portion severed from the web, and the portion conveyed for further processing. Turning now to the drawings, FIG. 1 illustrates a front elevation view of a first embodiment 1 of an apparatus according to the present invention. The apparatus 1 preferably includes a transfer mechanism 3 and a cutter 5. Such apparatus 1 is generally disclosed in detail in U.S. Pat. No. 7,795,584, which is incorporated herein by reference in its entirety.

Figure 2A:
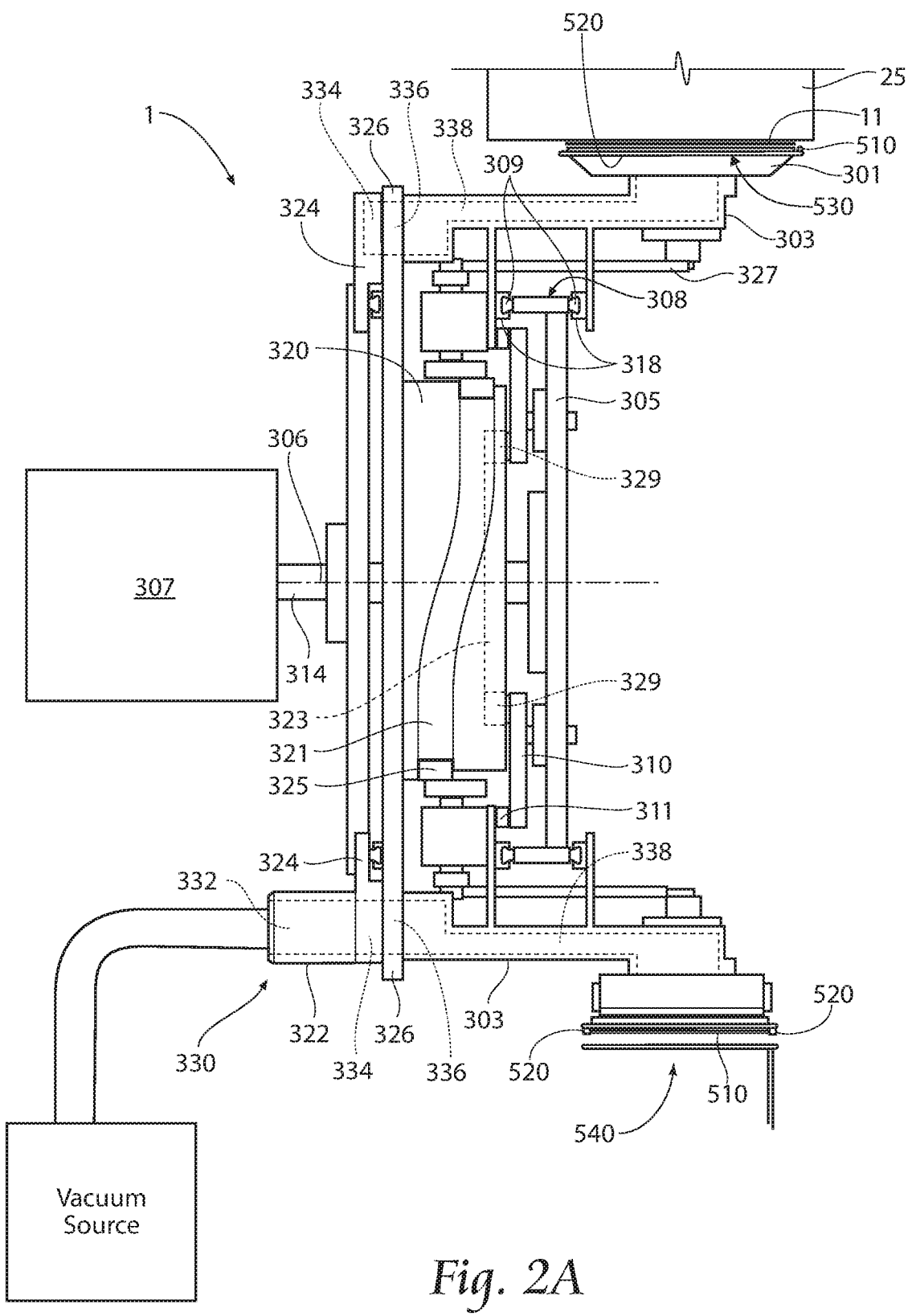
FIG. 2A is a top plan view of the embodiment of FIG. 1.

Referring also to FIG. 2A, the transfer mechanism 3 includes a plurality of pucks 301. Each puck 301 has a leading edge 302 and a trailing edge 304 and is coupled to a puck support 303, which is ultimately rotated by a puck wheel 305 about a puck transfer axis 306, which is a major axis of rotation, through a transfer path 4. As used throughout the description of the preferred embodiment, "rotate" and its variants refer to the movement of an entire puck 301 and puck support 303 assembly about the transfer axis 306, while "spin" and its variants refer to the radial spin of a puck 301 about a puck spin axis 312, which is substantially perpendicular to the puck transfer axis 306. The puck wheel 305 is driven preferably by a substantially operationally constant rotational force provided by a shaft 314 coupled to a motor 307.

As seen in FIG. 2A, the apparatus 1 may also include a manifold 330 to allow fluid communication between a vacuum supply and the pucks 301 at certain positions. The manifold 330 is preferably comprised of a vacuum port 322, a stationary vacuum manifold 324 and a rotating vacuum manifold 326. The vacuum port 322 preferably provides vacuum connection point, which may be standard or custom. The port 322 provides a support structure and an aperture 332 to allow vacuum pressure to be drawn through the port 322. The stationary vacuum manifold 324 is generally a fixed plate having at least one vacuum groove 334 formed therethrough at a predetermined location. The vacuum groove 334 is stationary and in fluid communication with the vacuum port aperture 332. The rotating vacuum manifold 326 is generally a rotating plate preferably having a face in slidable relation to the puck supports 303. The rotating manifold 326 includes at least one aperture 336 to allow, when in fluid communication with the aperture 334 in the stationary manifold 324, a vacuum to be drawn through the vacuum port 322, the stationary manifold 324, the rotating manifold 326, the puck support 303 and the puck 301.

Although the terms "circumferential" and "rotation" are used to describe the transfer movement of the pucks 301, it is to be understood that the invention is not limited to applications utilizing a circular motion. For instance, rather than be driven by a puck wheel 305 rotated by a motor 307, the pucks 301 may be coupled to a chain drive (not shown) or something similar. The travel path of the pucks 301 may then be defined by the shape of an employed cam plate 320 or by the path of any supporting pitch rails 309 used.

Other components of the apparatus 1, generally, such as the pitch and spin linkages, etc., is provided in more detail in U.S. Pat. No. 7,795,584, but is not limiting upon the operation of the cutters described herein. That said, it may be advantageous to utilize some nonmagnetic components (or as many as possible) for use in the apparatus 1 within the transfer path 4, where such components may be exposed to an inductive cutting trigger, as further described below.

Figure 3:
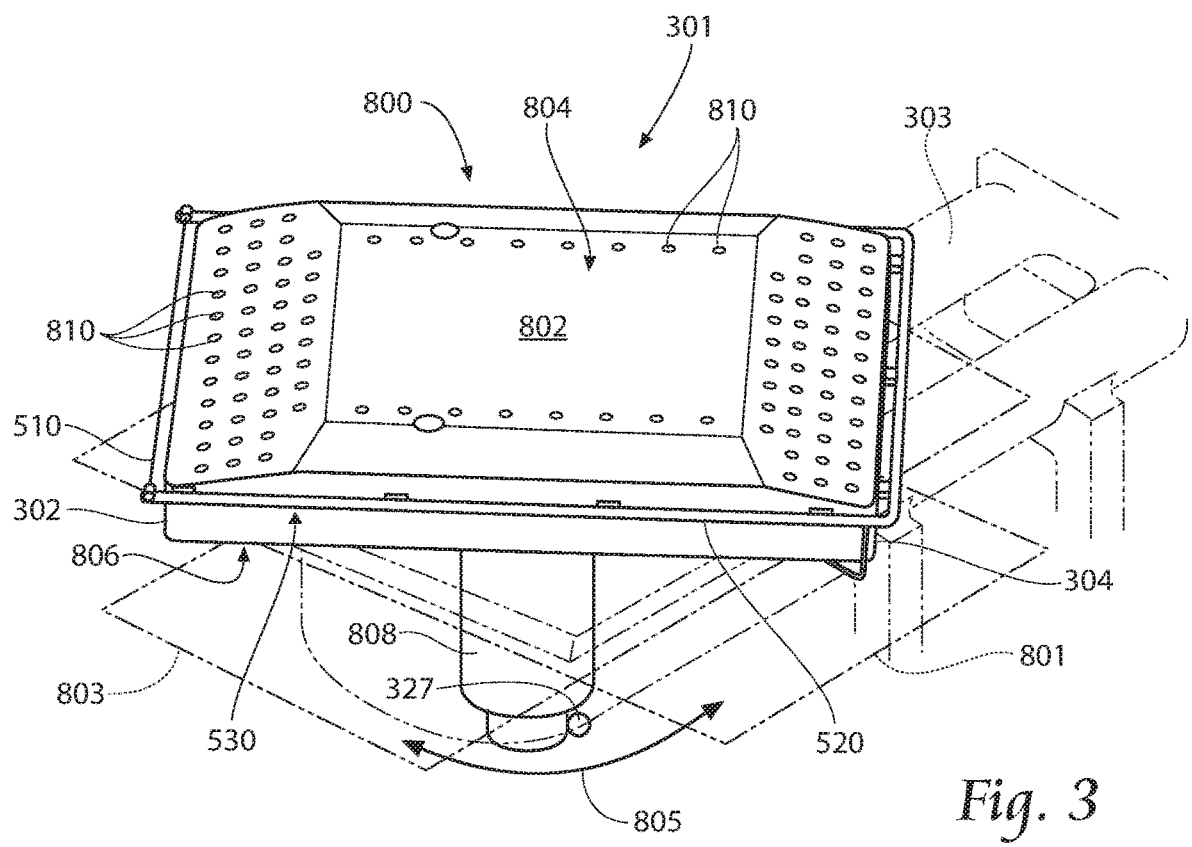
FIG. 3 is a perspective view of an embodiment of a puck member according to the present invention.

As an alternative to the anvil/knife cutter of U.S. Pat. No. 7,795,584, a preferred cutter 5 according to the present invention offers alternatives for cutting or perforation of the web 10. FIG. 3 provides a first, embodiment 800 of a preferred puck 301 according to the present invention. The puck 800 has a puck body 802 having a first web surface 804, a support surface 806 preferably oppositely disposed from the web surface 804, and a bearing shaft 808 depending from the support surface 806. The puck body 802 includes a vacuum chamber (not shown) within the body 802. Communicating fluidly with the vacuum chamber are preferably a plurality of web vacuum holes 810 extending through the web surface 804 and a plurality of support vacuum holes (not shown) extending through the support surface 806. The web vacuum holes 810 are provided about the web surface 804 and may be evenly spaced and provided near the perimeter of the web surface 804. The support vacuum holes provide a means for drawing a vacuum through the web vacuum holes 810 and the vacuum chamber in the puck body 802. By imparting a force to the bearing shaft 808, the puck 301 may be spun from a web-receiving orientation 801 to a web-placement orientation 803.

Figure 2B:
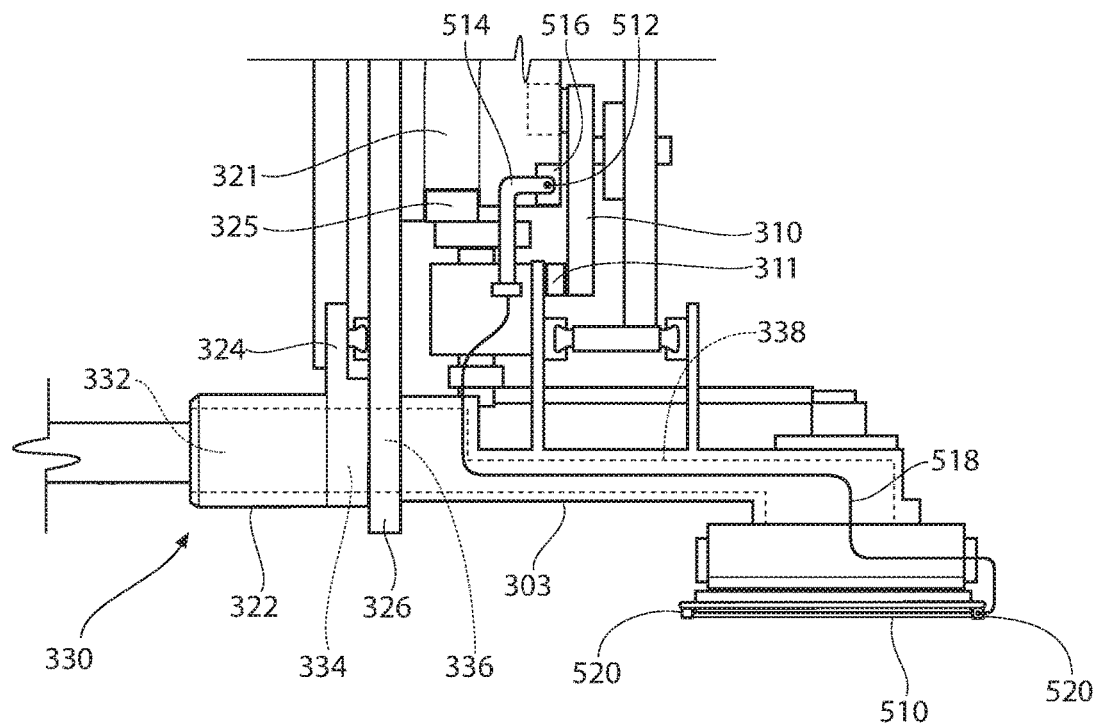
FIG. 2B is a top plan view of an alternate embodiment of a system according to the present invention.

Additionally, with reference to FIGS. 1-3, a first preferred cutter 5 includes a wire 510 carried on or proximately with the puck 301, extending along a majority of, and at a predetermined angle (including 0-90 degrees) with respect to, the puck's leading edge 302 and/or trailing edge 304. The wire 510 is preferably electrically coupled to and supported by an electrically conductive cutter yoke 520, the wire 510 and the yoke 520 forming a cutting loop 530 of electrically conductive material. The cutting loop 530 is preferably disposed within the transfer path 4. The wire 510 preferably provides a higher electrical resistance than the remainder of the cutting loop 530.

Inductively cooperating with the cutting loop 530 is a trigger loop 540, spaced from the traveling web 10 (preferably by a distance of about 0.25 inches to about three inches, with about one inch to about two inches being more preferred), and disposed outside of the transfer path 4. The trigger loop 540 comprises one or more loops of conductive material coupled to a power supply. The trigger loop 540 is preferably approximately similar in size and shape to the cutting loop 530. In this fashion, the trigger loop 540 is configured to operate as an inductive loop, generating a magnetic field, which in turn generates an electrical current in the cutting loop 530. The resistive nature of the wire 510 causes it to heat up in response to the generated electrical current to a temperature that effects a perforation or cut of the web 10 to form the insert pad 11, at least when the wire 510 touches the web 10. A preferred temperature for cutting the web 10 may be at least about 200 degrees Celsius, and up to about 400 degrees Celsius, which may cut the web 10 with exposure to such heat for a cut time of about 0.05 seconds to about 0.20 seconds, with about 0.10 seconds being most preferred.

Figure 3A:
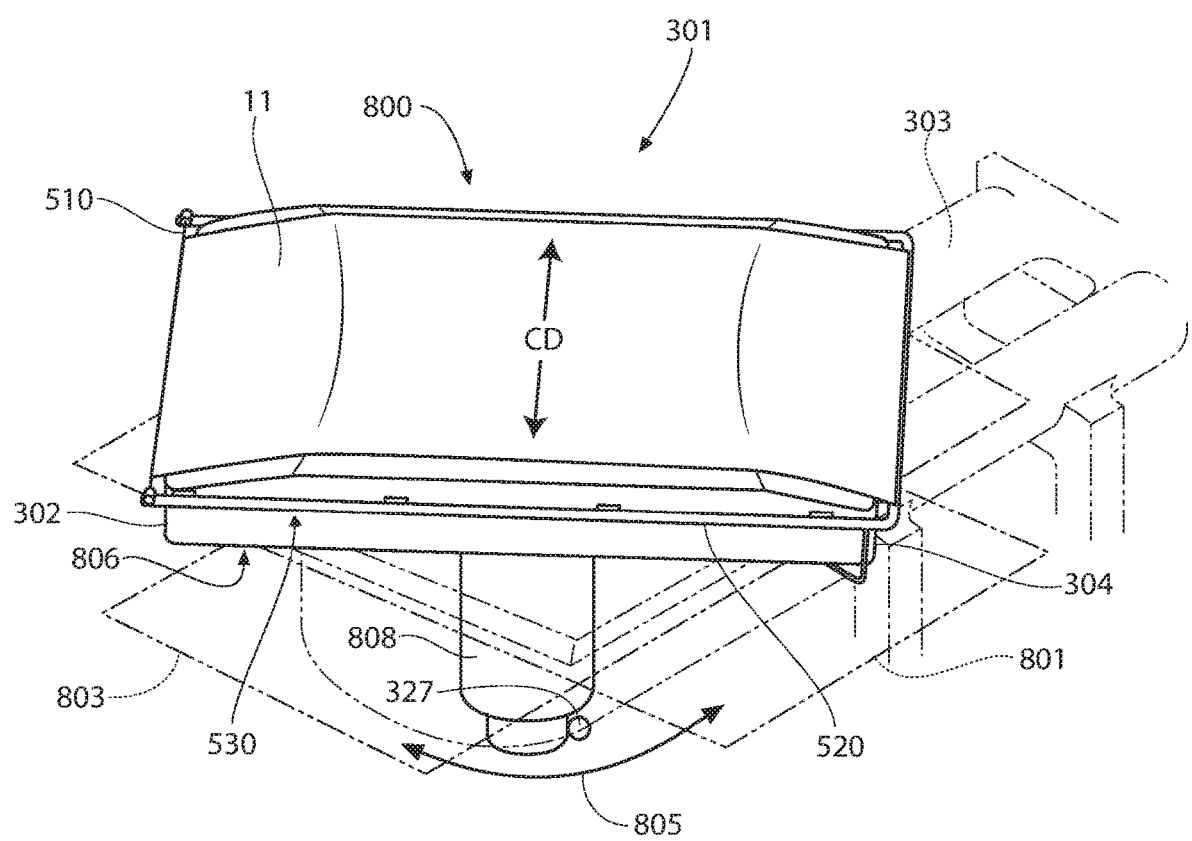
FIG. 3A is a perspective; view of an embodiment of a puck member showing a cross machine direction.

While the wire 510 is shown in an at least substantially straight-line configuration, tensioned between inapposite portions of the yoke 520, other wire path configurations are anticipated, such as serpentine, sawtooth, and/or two-dimensional or three-dimensional geometric shapes. While the wire 510 may lie in a geometric plane that is at least substantially parallel with the web surface 804 of the respective puck 301, or parallel with a plane that is tangent to the transfer path 4, such arrangement is preferred for cutting the web 10. Additionally or alternatively, if the web 10 is intended to be modified (as opposed to perforated or cut) by the heated wire 510, portions of the wire 510 or the complete wire 510, may extend radially inwardly towards the puck, transfer axis 306. Such arrangement will create areas along the length of the wire 510 that are a different realized temperature at the surface of the web 10, which may enable modification of the web 10, such as embossing, sealing, etc. Multiple raised points of the wire 510 (such as a coiled wire) can also be employed to create a perforated effect on the web. If desired, a perforated web can be accelerated at a point desired downstream in order to cut the web across a cross-machine direction of the web (see for example cross direction CD of FIG. 3A).

Alternatively, the wire 510 can be supplied with electrical current directly, as opposed to having a current induced by the trigger loop 540, thereby eliminating the need for the loop 540. If electrical current is to be supplied directly to the wire 510, it may be done continuously, or current may be electrically or mechanically timed, such as by using the alternate embodiment shown in FIG. 2B. In this arrangement, a wiper contact 512 is supported on a wiper arm 514, which is directly or indirectly affixed to the puck support 303. An electrically energized swipe plate 516 is disposed on or integrally formed with the cam plate 320. The wiper contact 512 is electrically coupled to the cutting wire 510 by a preferably insulated, electrically conductive wire 518, which may be connected to the cutting yoke 520. In this fashion, as a puck 301a travels around the transfer axis 306, the wiper contact 512 will travel about the cam plate 320 and engage the swipe plate 516 at the appropriate time to allow the resistive cutting wire 510 to heat up to a sufficient temperature to accomplish a predetermined cut, perforations (see for example FIG. 14A), or modification of the web 10. Also, although the cutting wire 510 is shown internal to the transfer path 4, it is to be understood that the cutting wire 510 may approach the web from outside of the transfer path 4 and travel through the path 4 between adjacent pucks 301.

The wire 510 may be any preferred conductive/resistive material, such as copper, and may be treated to avoid adhesion to the web 10, such as by being a Teflon® coated wire or nichrome wire.

In order to control the temperature of the wire 510, several variables can be controlled. First, dwell time, or the amount of time the wire 510 or cutting loop 530 is under the influence of trigger loop 540, can be controlled. The faster that the wire 510 is rotated, the more energy from trigger loop 540 will be required, if all other variables are equal. The size of trigger loop 540 can be increased or decreased, and the number of loops of conductive material coupled to a power supply can be increased or decreased. The physical size of the loop 540 can be increased as measured for instance by a period of degrees about the revolution of pucks P1, and the loops 540 can be provided about a greater or lesser amount of rotation of pucks P1. The loops 540 can be variably spaced from the traveling web 10 to alter the energy transmission as well. The strength of the induction field can be matched to machine speeds in a preferred embodiment, with the strength of the induction field in a preferred embodiment proportionate to speed of the machine. Variable power can also be applied to the loops 540 to control the strength of the induction field. For instance, at a machine jog or thread speed (generally slower than full production speed), it would be preferred to have a lower strength induction field to avoid undesired damage to traveling web 10. If several loops 540 are positioned, one or more could be activated depending on strength demands, related to speed, with higher speeds resulting in smaller dwell times and thus higher demand during that smaller dwell time period. The spacing between loop or loops 540 relative to the web 10 could also be varied, and energy applied to loops 540 varied.

Other methodologies of employing a heated component for severing a pad 11 from a traveling web 10 include static discharge and/or one or more lasers. A static discharge cutting approach has been demonstrated with one or more point source sparks cutting/perforating a web material contacted by such sparks. It is estimated that a plurality of point source sparks may be utilized to sufficiently cut a web 10, or at least sufficiently perforate the web 10, to allow separation of a pad 11 by application of a circumferential tearing force. Sheet or web material may also be perforated or severed along a line or other pattern in a machine direction, or in a direction at an angle to the machine direction, by one or more lasers.

All of the components of the apparatus 1 can readily be made of standard materials. For example, the supporting and rotating structures, such as the puck supports 303, linkages, wheels, etc., may be made of suitable aluminum. The pucks 301 are formed from any desirable material, but a lightweight material is preferred, such as nylon.

An exemplary apparatus and operation can be explained with reference to FIGS. 1-10. Generally, the apparatus 1 receives a continuous web 10, separates a section from the continuous web 10 to form an insert or pad 11, and may alter the orientation of the pad 11, such as by spinning the pad 11 to a predetermined angle and/or changing the pitch between consecutive pads 11. While the operation of the apparatus 1 is described with reference to a single puck 301 a, it is to be understood that the operation of the remaining pucks 301 is at least substantially similar. Furthermore, although the operation is described with reference, in FIGS. 4-11, to discrete puck positions P1-P8, it is to be understood that the operation is preferably generally continuous. The discrete positions aid in illustrating the operations being performed.

Figure 4:
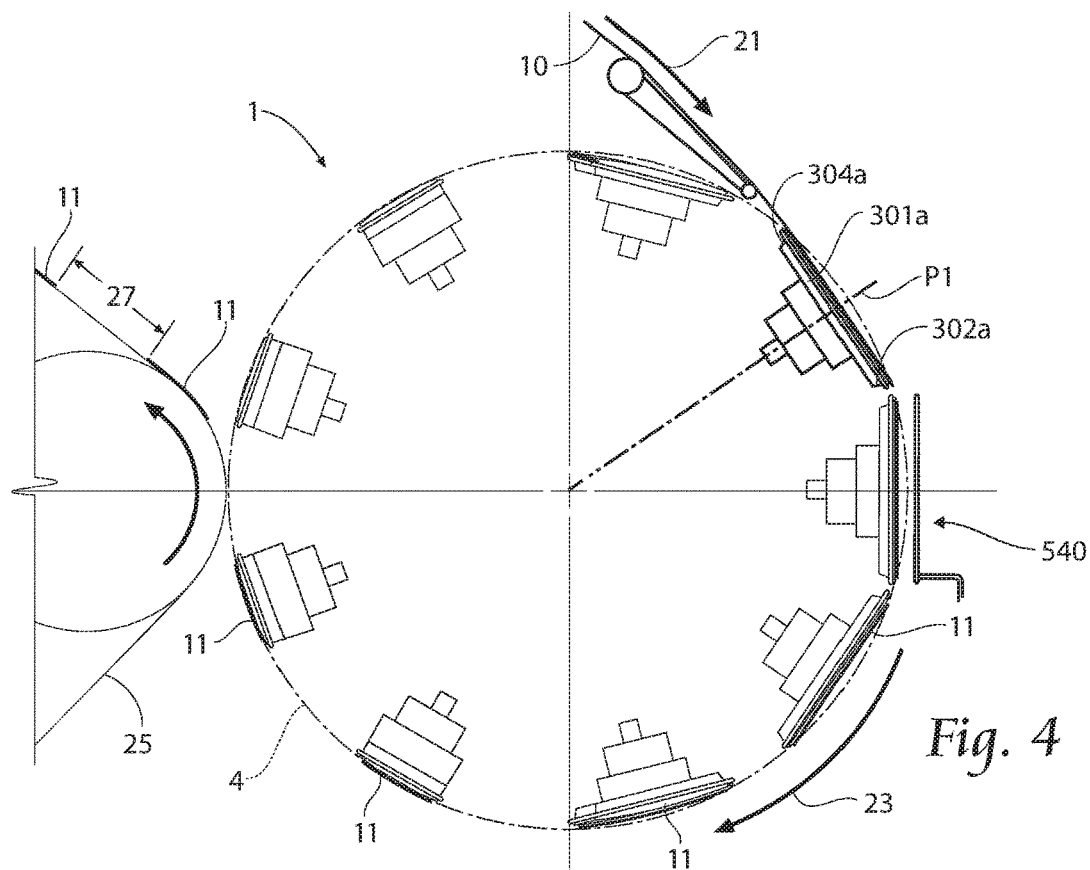
FIG. 4 is a front elevation view of the embodiment in FIG. 1 in a first position, eliminating some detail to better illustrate functionality.

FIG. 4 shows a representative puck 301a in a first position P1. In the first position P1, the puck 301a receives continuous web material 10 traveling in a first direction 21 at the first velocity. A vacuum is drawn through the vacuum port 326, the stationary vacuum manifold 322, the rotating vacuum manifold 324, the puck support 303 and the puck 301a to support the material 10 on the puck 301a surface. While receiving the web 10, the puck 301a is traveling about a puck wheel axis 306 in a second direction 23, to which at this point PI the first direction 21 is preferably substantially tangential. The puck 301a continues to move in the second direction 23 into a second position P2.

Figure 5:
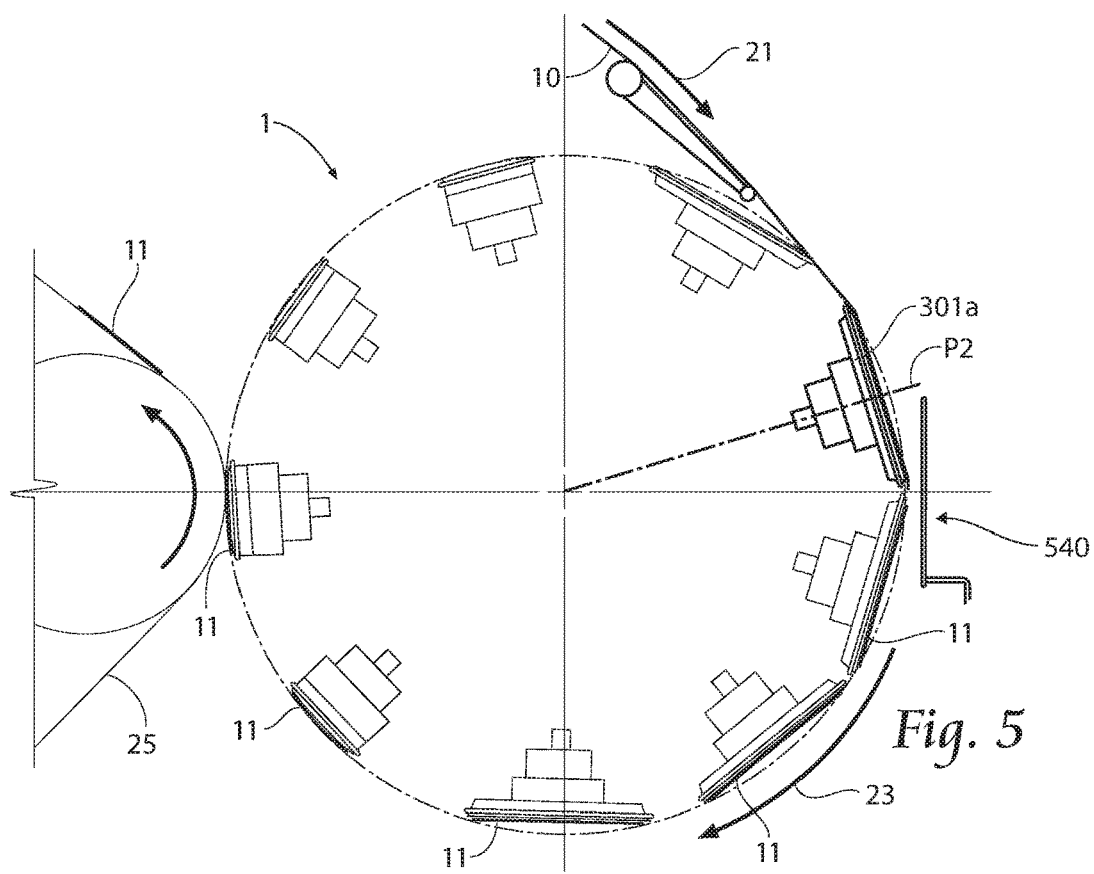
FIG. 5 is a front elevation view of the embodiment in FIG. 1 in a second position, eliminating some detail to better illustrate functionality.

FIG. 5 depicts the puck 301a in the second position P2, Here, the cutting coil 530 begins to enter the magnetic field generated by the trigger coil 540. The puck 301a proceeds to travel in the second direction 23 to substantially align the cutting coil 530 with the trigger coil 540 in a third position P3.

Figure 6:
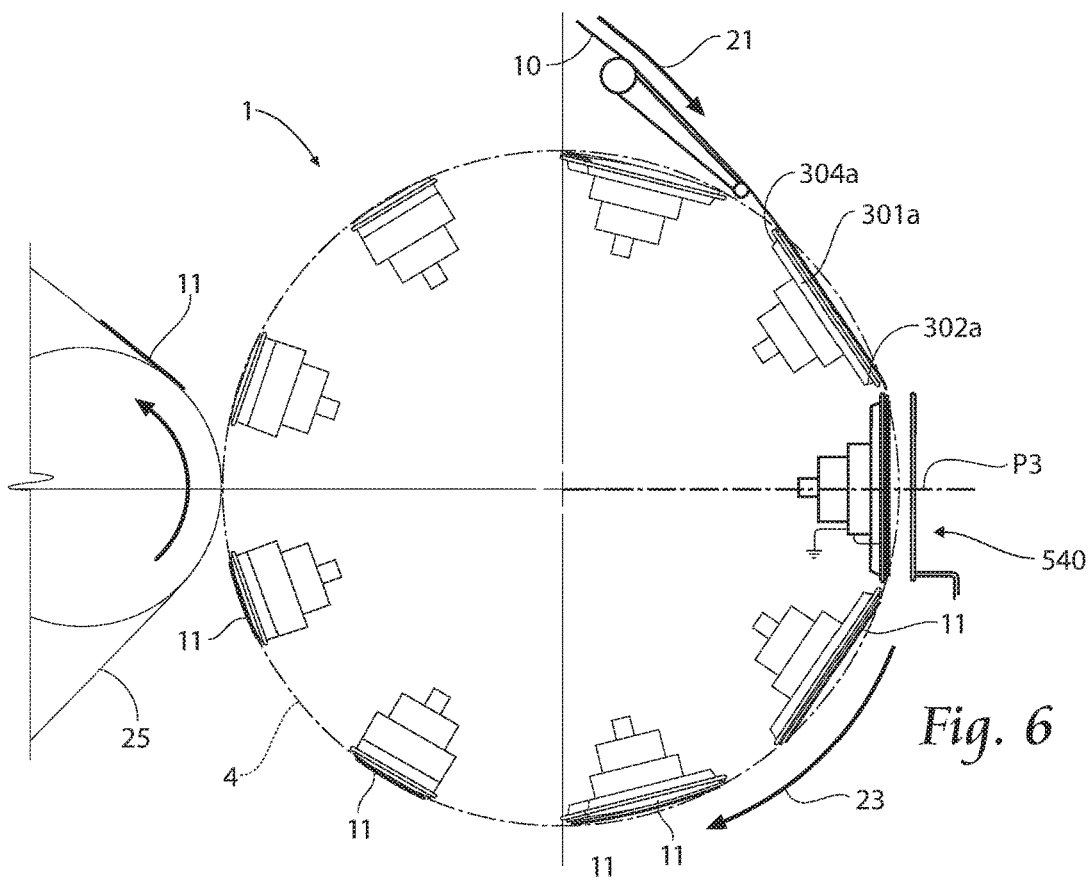
FIG. 6 is a front elevation view of the embodiment in FIG. 1 in a third position, eliminating some detail to better illustrate functionality.

FIG. 6 shows the puck 301a in the third position P3. In this position P3, the cutting loop 530 is preferably at least substantially parallel to the trigger loop 540, thereby maximizing the effect of the magnetic field generated by the trigger loop 540 and maximizing the current generated in the cutting loop 530. The wire 510, heated to an effective temperature, operates to cut and/or modify the web 10 proximate the leading edge 302 a and/or trailing edge 304a of the puck 301a to cut a section 11 a from the web 10. The section 11 a is held to the puck 301a by the vacuum, which was drawn previously. After the cut and/or modification, the puck 301a travels in the second direction 23 to a fourth position P4.

Figure 7:
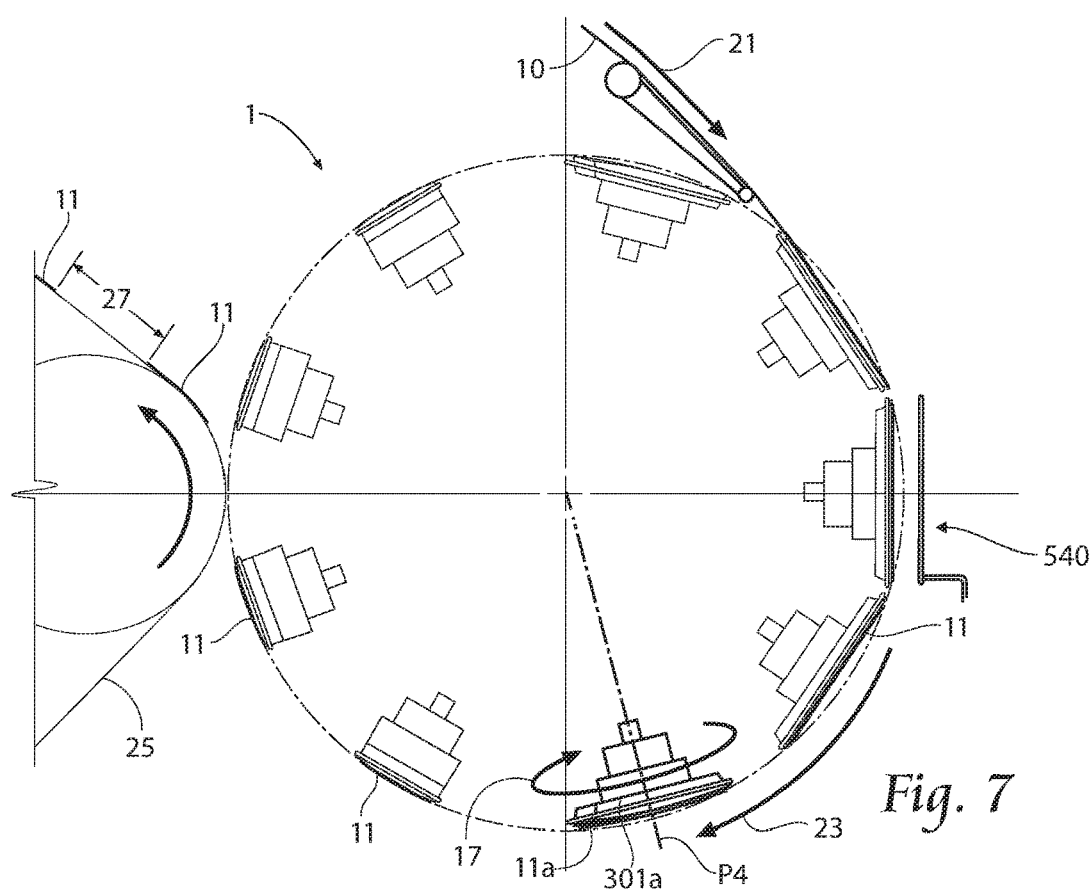
FIG. 7 is a front elevation view of the embodiment in FIG. 1 in a fourth position, eliminating some detail to better illustrate functionality.
Figure 11:
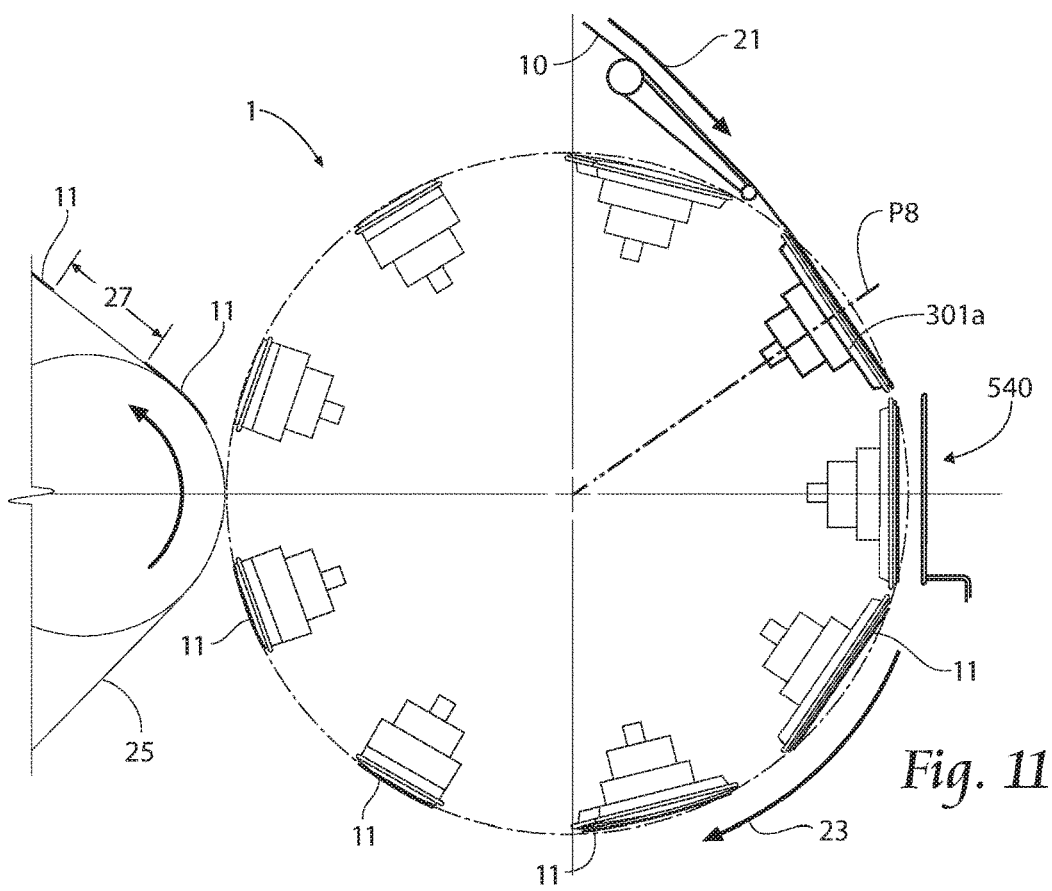
FIG. 11 is a front elevation view of the embodiment in FIG. 1 in an eighth position, eliminating some detail to better illustrate functionality.

FIG. 7 shows the puck 301a in the fourth position P4. As mentioned previously, it is often desirable to spin the cut section 11 a to some predetermined angle prior to placement on a receiving surface 25. Here, the puck 301a is shown while in the midst of a spin. While FIG. 11 shows the puck 301a rotating in the fourth position P4, the puck 301a may rotate in a third direction 17 to a desired angle any time after the pad 11 is severed from the web 10, preferably before placement onto the receiving surface 25 or otherwise being removed from the puck 301 a. Alternatively, the section 11 a does not have to be spun at all.

Besides rotation and spin of the pucks 301, the apparatus 1 may also change the circumferential spacing of the pucks 301 a; thereby resulting in a placement pitch that is different from the pitch at which the web material 10 was cut. The ultimate circumferential spacing of the pucks 301 at the receiving surface 25 is a function of a desired placement pitch 27 and the speed at which the receiving surface 25 is traveling. In the preferred embodiment, the circumferential spacing is achieved by a desired pitch cam slot 323 configuration. Upon achieving desired circumferential spacing, the puck 301a arrives in a fifth position P5.

Figure 8:
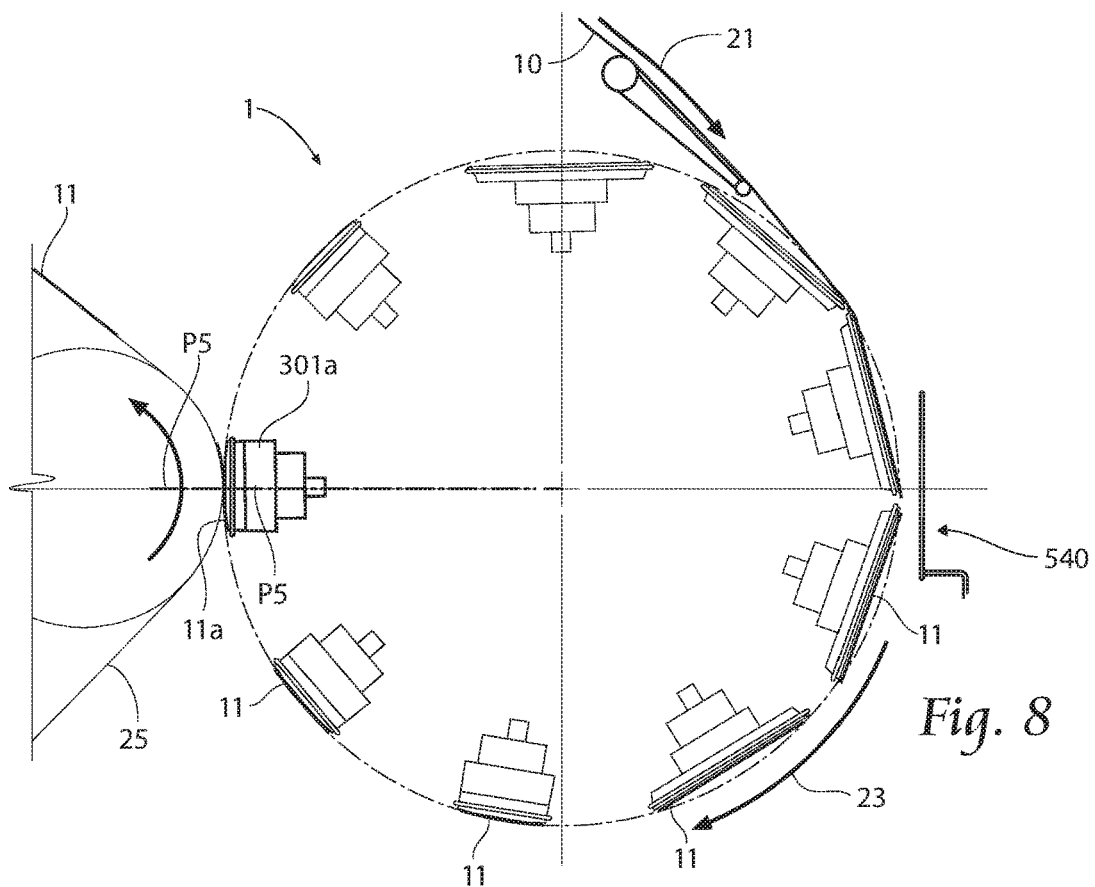
FIG. 8 is a front elevation view of the embodiment in FIG. 1 in a fifth position, eliminating some detail to better illustrate functionality.

The puck 301a is shown in the fifth position P5 in FIG. 8. The puck 301a has been situated at the correct placement pitch or distance 27 with respect to the puck 301 that preceded it 301 a. At this pitch or distance 27, the section 11 a is transferred to the receiving surface 25. At the time of placement, the vacuum that was drawn through the puck support 303 and puck 301a may be removed from at least a portion of the puck 301 a, thereby allowing a smooth transfer of the cut insert 11 a from the puck 301a to the receiving surface 25. The vacuum may remain active through the stationary vacuum manifold 322 and the rotating vacuum manifold 324 to assist in supporting subsequent sections 11 in place on later neighboring pucks 301. After placing the section 11 a onto the receiving surface 25, the puck 301a continues in the second direction 23 to a sixth position P6.

Figure 9:
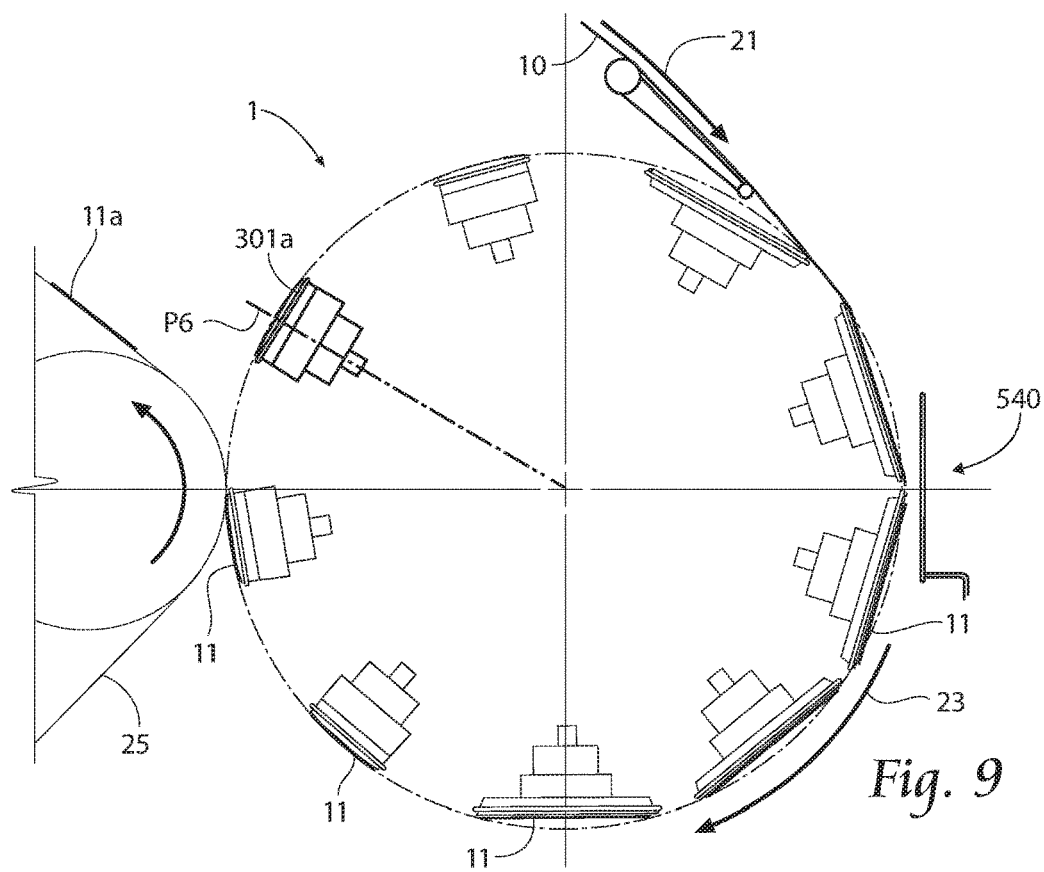
FIG. 9 is a front elevation view of the embodiment in FIG. 1 in a sixth position, eliminating some detail to better illustrate functionality.

FIG. 9 shows the puck 301a in the sixth position P6. The puck 301a is shown as having released the cut section 11 a onto the receiving surface 25. The puck 301a continues to move in the second direction 23 to a seventh position P7.

Figure 10:
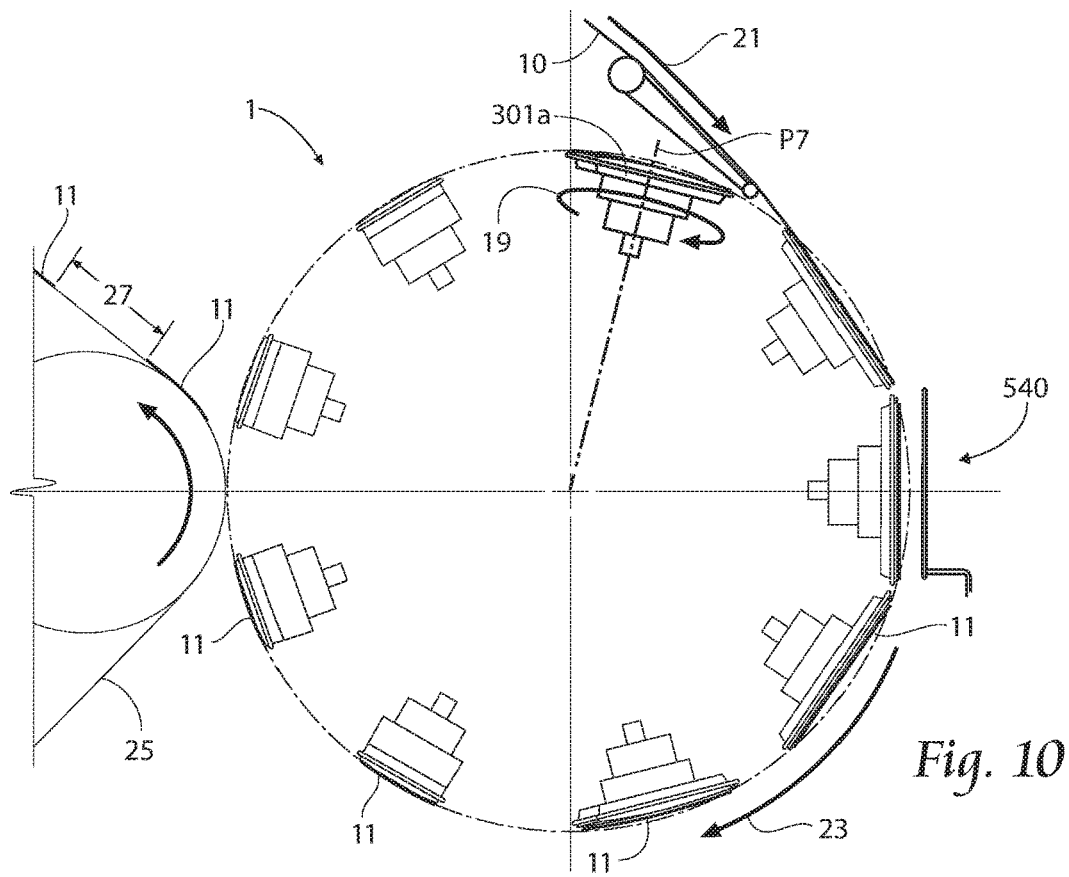
FIG. 10 is a front elevation view of the embodiment in FIG. 1 in a seventh position, eliminating some detail to better illustrate functionality.

FIG. 10 depicts the seventh position P7 of the puck 301 a. If the puck 301a and pad 11 a were spun after cutting to some predetermined angle prior to placement on the receiving surface 25, the puck 301a may need to be adjusted to a web-receiving orientation. While FIG. 10 shows the puck 301a spinning in the seventh position P7, the puck 301a may spin in a fourth direction 19 any time after the section 11 a has been placed on the receiving surface 25 and before the continuous web 10 is received. The fourth direction 19 may be the same as the third direction 17 or opposite.

Finally, the puck 301a is shown in the eighth position P8 in FIG. 11. The eighth position P8 is substantially similar or identical to the first position P1.

Figure 12:
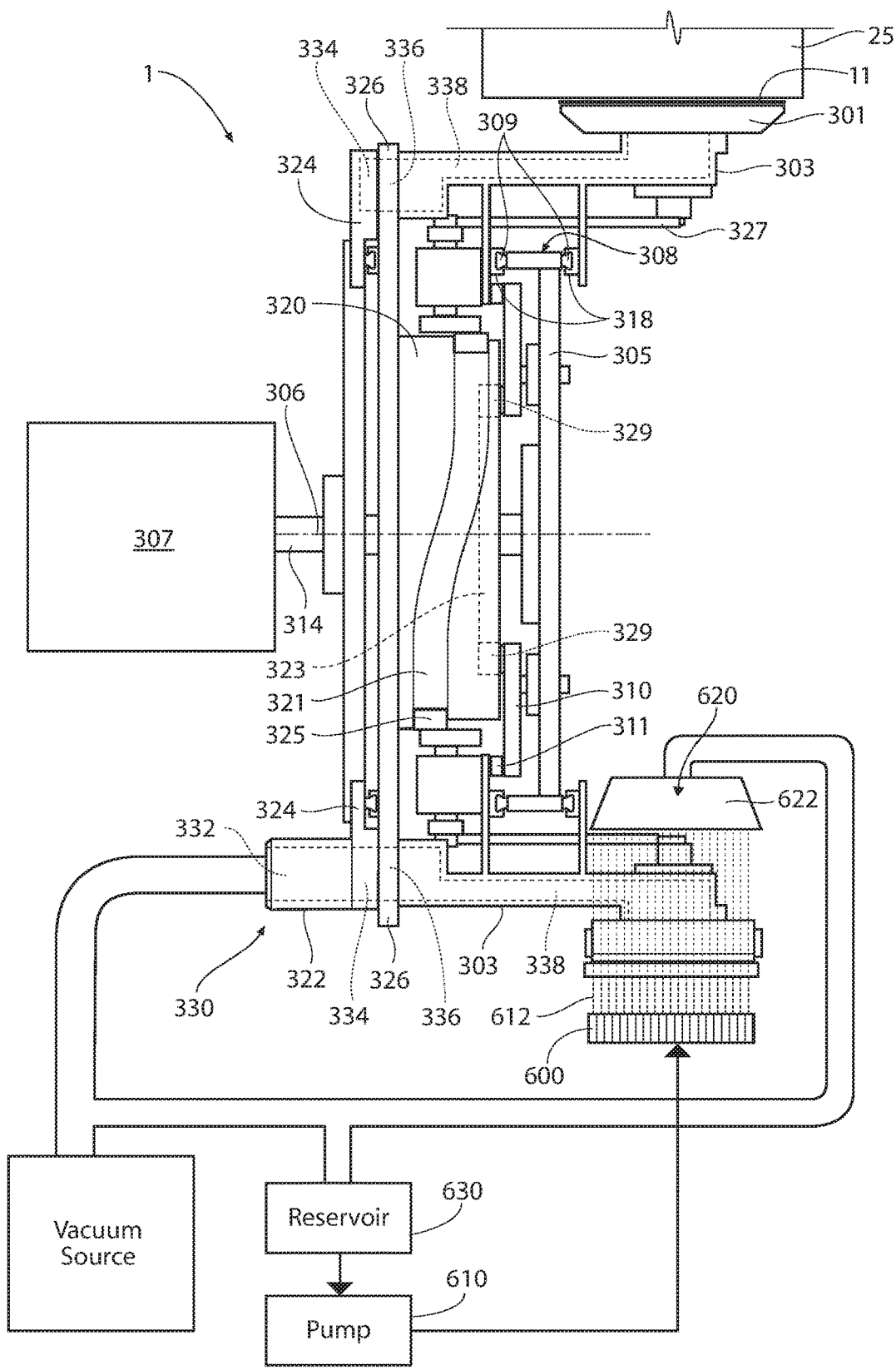
FIG. 12 is a top plan view of a second embodiment of an apparatus according to the present invention.

Another option for cutting pads 11 from the continuous web 10 is to utilize one or more fluid jets, as depicted in FIG. 12. In the embodiment shown, one or more fluid jets 600 may be fed by a pump 610. The jets 600 may be mechanically or electrically timed to eject a predetermined amount of fluid 612 in a predetermined fluid pattern (e.g. stream, spray, curtain) to sever pads 11 from the web 10. Examples of acceptable fluid 612 may be water, superheated steam, and/or air. Where water is utilized, a preferred collection system 620 may be desirable. The collection system 620 includes a fluid collection hood 622 situated internal to the transfer path 4 and adapted to collect a majority of the ejected fluid 612. Such hood 622 may be coupled to the vacuum source, or a separate vacuum source, and collect the fluid 612 in a reservoir 630 to feed the pump 610.

Figure 13:
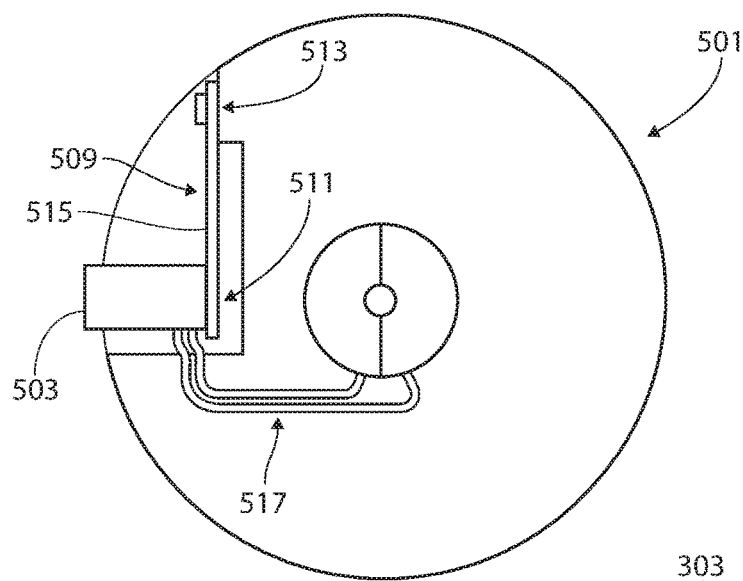
FIG. 13 is a front elevation, partial cross-section view of an embodiment of an anvil roller of an apparatus according to the present invention.

If mechanical cutting and/or perforation is desirable, improved options for such operations have been developed. For example, an ultrasonic horn/knife combination may be used, or even an improved anvil surface 503 provided on the anvil roller 501 of the apparatus 1 shown in U.S. Pat. No. 7,795,584. FIG. 13 provides an improved anvil roller 501, which may be used. In this embodiment, the anvil surface 503 is radially moveable with respect to the roller 501. The radial mobility is provided with a cantilever mount arrangement 509 having the anvil surface 503 mounted at a free end 511 opposite a fixed end 513 of a cantilever arm 515, having preferred deflection characteristics. In certain applications, the web 10 may have an adhesive applied to at least one side of it, and that side may be the one contacted by the anvil surface 503. If mechanical contact between the surface 503 and the adhesive side of the web 10 is expected, then contamination of the surface 503 from built up adhesive may be an issue. It may be desirable, if the adhesive is applied upstream from the cutting operation, the adhesive properties of the adhesive may be interrupted prior to or during the cut, such as: deactivating the adhesive at a predetermined cut location on the web 10, applying a water mist to the anvil 503 and/or the adhesive, shielding the adhesive from the surface 503, such as by covering the adhesive with a non-adhesive talc or other inorganic material, and/or cross-linking the adhesive, such as by using light energy. Additionally or alternatively, the adhesive may be activated only after the contact with the anvil surface 503, or a cured adhesive may be used. Additionally or alternatively, the anvil surface 503 may be prepared to lessen the likelihood of adhesive contamination. For instance, the surface 503 may be coated with, or treated to form, a nonstick coating, such as Teflon®, an anodized surface, etc. Additionally or alternatively, the anvil surface 503 may be heated or chilled by introducing a heated or chilled fluid through fluid supply lines 517.

Figure 14:
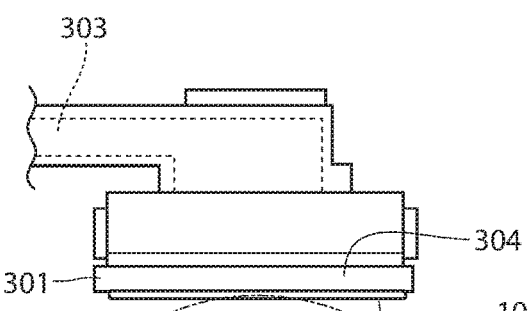
FIG. 14 is a partial top plan view of a third embodiment of an apparatus according to the present invention.
Figure 14:
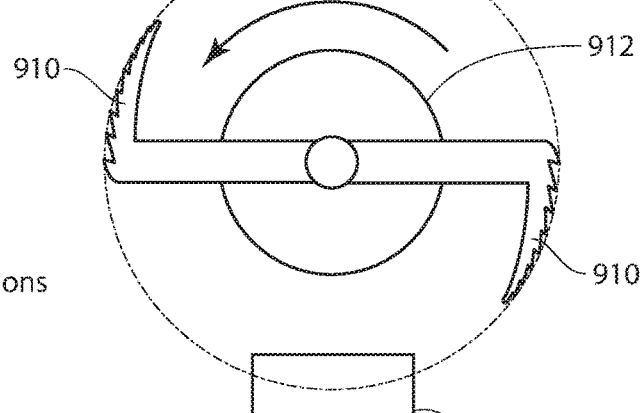
Figure 14A:
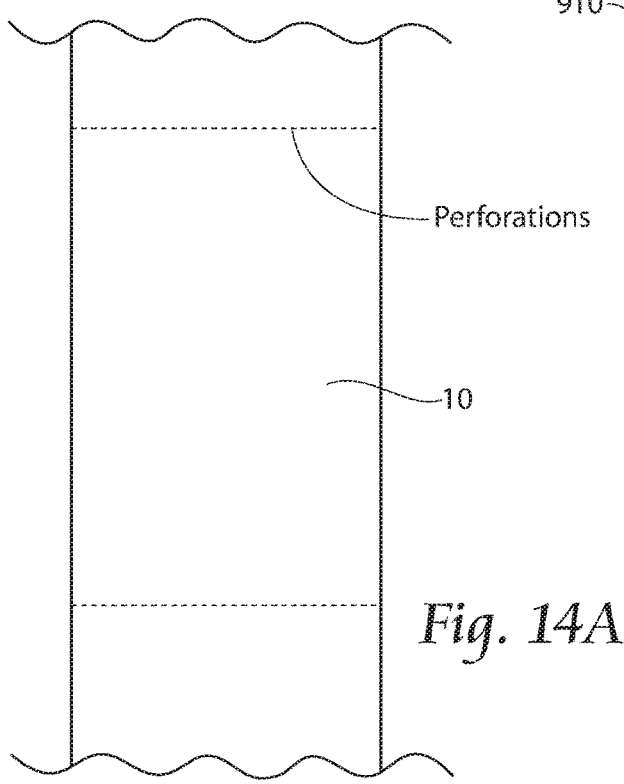
FIG. 14A is a partial top plan view showing one embodiment of the present invention in which perforations are formed.

FIG. 14 depicts another mechanical cutting operation using one or more knife blades, such as serrated knife blades 910. Preferably each knife blade 910 is mechanically or electrically timed (such as by a knife motor 912) to strike the web 10 in a manner similar to a scythe at or near the speed of the web 10. In this fashion, the web 10 may be completely severed, but the web 10 is at least perforated by the blade and continued travel of the puck 301a will tear the pad 11 from the web 10.

In certain applications, the web 10 may have an adhesive applied to at least one side of it, and that side may be the one contacted by the blades 910. If mechanical contact between a blade 910 and the adhesive side of the web 10 is expected, then contamination of the blade 910 from built up adhesive may be an issue. It may be desirable during the path of travel of each blade 910 that it be treated by a blade preparation unit 914. The blade preparation unit 914 may perform functions on the blade 910, such as heating, cooling, cleaning, sharpening, etc., so as to lessen the likelihood of adhesive contamination. Additionally or alternatively, the blade(s) 910 may be prepared to lessen the likelihood of adhesive contamination. For instance, each blade 910 may be coated with, or treated to form, a nonstick coating, such as Teflon®, an anodized surface, etc.

The foregoing is considered as illustrative only of the principles of the invention. Furthermore, since numerous modifications and changes will readily occur to those skilled in the art, it is not desired to limit the invention to the exact, construction and operation shown and described. For example, though depicted as cutting a continuous web, it should be understood that, such inductive activation of a heated element may be used to cut, perforate, or emboss an individual article, which may be supported on a puck, or like mechanism. In this way, such article is modified in some fashion instead of or in addition to being separated from an end of a continuous web. While the preferred embodiment has been described, the details may be changed without departing from the invention, which is defined by the claims.

What is claimed is:

1. A system for processing a web of material, the system comprising:
    a wheel configured to rotate about an axis;
    a traveling body coupled to the wheel and configured to carry a web; and
    a cutting loop coupled to the traveling body and configured to receive electrical current, wherein the web of material is disposed adjacently to the cutting loop;
    wherein the cutting loop is configured to:

receive the electrical current in a web alteration zone to heat the cutting loop; and contact the web of material in the web alteration zone to alter the web of material from a first condition of the web to a second condition of the web.

2. The system of claim 1, wherein the cutting loop is configured to receive the electrical current according to a mechanical timing.

3. The system of claim 2 further comprising:
a wiper contact coupled to the wheel and electrically coupled to the cutting loop; and
a swipe plate coupled to a stationary member and configured to supply the electrical current to the wiper contact to heat the cutting loop when electrically coupled with the wiper contact.

4. The system of claim 3, wherein, in the web alteration zone, the swipe plate is electrically coupled with the wiper contact sufficiently to allow the cutting loop to heat up to a temperature to accomplish the alteration of the web material.

5. The system of claim 1, wherein the traveling body comprises a puck.

6. The system of claim 1 further comprising:
a vacuum system;
wherein the traveling body comprises:
a vacuum chamber fluidly communicating with the vacuum system; and
a plurality of vacuum holes in a surface of the traveling body, the plurality of vacuum holes fluidly communicating with the vacuum chamber; and
wherein the vacuum system is configured to create a vacuum in the vacuum to cause the traveling body to carry the web.

7. The system of claim 1, wherein the cutting loop is configured to contact the web of material in the web alteration zone to one of:
sever a pad from the web; and
form perforations in the web.

8. A system for processing a web of material, the system comprising:
a rotatable puck support assembly;
a puck coupled to the rotatable puck support assembly and configured to carry a web; and
a cutting loop coupled to the puck and configured to receive electrical current, wherein the web of material is disposed adjacently to the cutting loop;
wherein the cutting loop is configured to:
heat to a cutting temperature in a web alteration zone; and
contact the web of material in the web alteration zone to sever a pad from the web.

9. The system of claim 8, wherein the cutting loop is configured to receive the electrical current in the web alteration zone to heat to the cutting temperature.

10. The system of claim 9, wherein the cutting loop is configured to receive the electrical current according to a mechanical timing.

11. The system of claim 9 further comprising:
a wiper contact coupled to the rotatable puck support assembly and electrically coupled to the cutting loop; and
a swipe plate coupled to a stationary member and configured to supply the electrical current to the wiper contact to heat the cutting loop when electrically coupled with the wiper contact.

12. The system of claim 11, wherein, in the web alteration zone, the swipe plate is electrically coupled with the wiper contact sufficiently to allow the cutting loop to heat up to cutting temperature.

13. The system of claim 8 further comprising:
a vacuum system;
wherein the puck comprises:
a vacuum chamber fluidly communicating with the vacuum system; and
a plurality of vacuum holes in a surface of the puck, the plurality of vacuum holes fluidly communicating with the vacuum chamber; and
wherein the vacuum system is configured to create a vacuum in the vacuum to cause the puck to carry the severed pad.

14. A system for processing a web of material, the system comprising:
a vacuum system;
a traveling body configured to carry a web, the traveling body comprising:
a vacuum chamber fluidly communicating with the vacuum system; and
a plurality of vacuum holes in a surface of the traveling body, the plurality of vacuum holes fluidly communicating with the vacuum chamber;
wherein the vacuum system is configured to create a vacuum in the vacuum to cause the traveling body to carry the web; and
a fluid jet system comprising:
one or more fluid jets; and
a fluid collection system;
wherein the web of material is disposed between the one or more fluid jets and the fluid collection system;
wherein the one or more fluid jets are configured to operate cooperatively with the fluid collection system in a web alteration zone to generate a cutting fluid; and
wherein the cutting fluid contacts the web of material in the web alteration zone to alter the web of material from a first condition of the web to a second condition of the web.

15. The system of claim 14, wherein the fluid comprises one of water, superheated steam, and air.

16. The system of claim 14, wherein the fluid collection system comprises a fluid collection hood positioned to collect the cutting fluid.

17. The system of claim 14, wherein the fluid collection system comprises a fluid collection hood fluidly coupled with the vacuum system and positioned to collect the cutting fluid; and
further comprising a reservoir fluidly coupled with the fluid collection hood and configured to contain at least a portion of the collected cutting fluid.

18. The system of claim 17 further comprising a pump fluidly coupled with the reservoir and with the one or more fluid jets and configured to deliver fluid contained in the reservoir to the one or more fluid jets.

19. The system of claim 14, wherein the web of material is further disposed between the one or more fluid jets and the traveling body.

* * * * *